United States Patent [19]

Bailey et al.

[11] 4,280,002

[45] Jul. 21, 1981

[54] MICROBIOLOGICAL GROWTH CONTAINER

[75] Inventors: Dale O. Bailey; Paul G. Honl, both of St. Paul, Minn.

[73] Assignee: Minnesota Mining and Manufacturing Company, St. Paul, Minn.

[21] Appl. No.: 99,319

[22] Filed: Dec. 3, 1979

[51] Int. Cl.³ .............................................. C12M 1/22
[52] U.S. Cl. ................................. 435/298; 435/296; 435/299
[58] Field of Search ............... 435/298, 296, 297, 299, 435/300, 301

[56] References Cited

U.S. PATENT DOCUMENTS

| 3,055,808 | 9/1962 | Henderson | 435/298 |
| 3,559,834 | 2/1971 | Taylor | 215/261 |
| 3,691,140 | 9/1972 | Silver | 526/271 |
| 3,696,958 | 10/1972 | Lee | 215/261 |
| 3,857,731 | 12/1974 | Merrill, Jr. et al. | 526/307 |

Primary Examiner—Robert J. Warden
Attorney, Agent, or Firm—Cruzan Alexander; Donald M. Sell; John C. Barnes

[57] ABSTRACT

A petri dish comprising a base and cover with a seal for the cover affording ingress and egress of air and restricting evaporation from the dish. The seal is formed by a monolayer of microsphere pressure-sensitive adhesive.

4 Claims, 3 Drawing Figures

MICROBIOLOGICAL GROWTH CONTAINER

FIELD OF THE INVENTION

This invention relates to an improved microbiological growth container such as a petri dish, and more particularly to an improved microsphere adhesive sealing structure for a container allowing the warm, aqueous based culture medium to remain in a moistened condition for extended periods of time but allowing the transfer of air through the seal, permitting growth of microorganisms on or in the growth media.

BRIEF DESCRIPTION OF THE PRIOR ART

The present invention relates to an improvement in microbiological growth containers, an example of which is a petri dish, to solve the problem of rapid evaporation and a drying of the culture medium, while at the same time permitting air flow through the seal which helps to prevent a deleterious accumulation of carbon dioxide within the petri dish resulting from the growth of the microorganism. Thus, it is desirable to allow air to move in and out of the dish at the same time restricting the escape of moisture vapors resulting from evaporation.

Some prior art such as U.S. Pat. No. 3,055,808, issued Sept. 25, 1962, to J. A. Henderson discloses a petri dish having an improved seal which hermetically seals the dish in such a way that unless there is a deliberate abuse of the dish, the cover will maintain the desired seal. In this structure the seal between the dish and the cover is adhesive in nature and preferably a pressure-sensitive and permanently tacky, adhesive which will withstand and remain tacky at temperatures ranging from 25° C. to 60° C. Examples of such adhesives are given in the patent and are identified as micro-crystalline wax having a melting point of between about 130° to 150° F. and a penetration (A.S.T.M. D-1321) of between 35 to 50, to which about 7-13% of an isobutylene polymer soluble in the molten wax is added. In this structure the coating of adhesive extends circumferentially along the upper peripheral edge of the dish and circumferentially along the inner surfaces of the outer periphery of the base walls, and the cover is formed of a material which is flexible enough to respond to lateral pressures applied to the side walls of the cover to release the seal between the cover and the dish. This prior art structure, however, does not permit the free egress and ingress of air from the petri dish but hermetically seals the dish against the flow of both air and vapors. The adhesive is characteristic of a film forming adhesive which is air and water vapor tight.

Prior art disclosing a seal affording some air movement but blocking the flow of vapors includes a study of a lot of the closure art, even closures such as used for wine where it is necessary to permit the bottle to breathe sufficiently for aging of the particular wine but not permitting the evaporation of the wine. One such patent is U.S. Pat. No. 3,559,834, issued Feb. 2, 1971 to W. S. Taylor. These structures wherein a seal formed of cork or other filter material is used between the cap and the container are multipart assemblies and do not afford the solution to sealing a shallow dish. Along this line, see also U.S. Pat. No. 3,696,958, issued Oct. 10, 1972 to H. M. Lee.

SUMMARY OF THE PRESENT INVENTION

Thus, it is believed that applicants have discovered a new sealing adhesive structure which may be utilized to seal shallow transparent dishes for microbiological studies such that growth of a microorganism will be permitted while restricting evaporation of the contents of the dish. The dish of the present invention comprises a shallow base having a bottom wall and side walls and a cover of a rigid transparent polymeric material having a lid with edge walls depending therefrom at a position sufficient to fit loosely on the base. A coating of a microstructure adhesive is applied to the inner surface of the cover adjacent the depending edge walls to be engaged by the upper surface of the side walls of the base and suitably adhere the cover to the base. The microstructure adhesive in a monolayer provides different sized adhesive microspheres or microglobules affording the passage of air from the dish but the structure (size, shape and position) of the adhesive microspheres are such that they restrict the flow of water vapor.

DESCRIPTION OF THE DRAWING

The present invention will be more fully described with reference to the accompanying drawing wherein.

DETAILED DESCRIPTION OF THE PRESENT INVENTION

Figure 1:
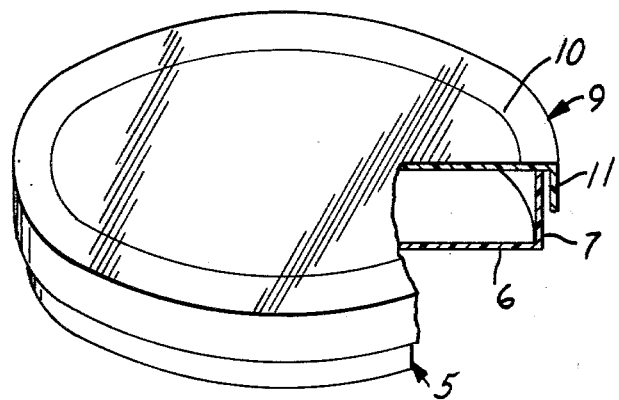
FIG. 1 is a perspective view of a petri dish constructed according to the present invention having one portion broken away to show the interior thereof.

The present invention relates to a microbiological growth container and as illustrated has a well known structure comprising a base 5 of shallow cylindrical configuration comprising a base wall 6 and projecting cylindrical side walls 7. The container also includes a cover having a circular configuration with a top 10 and depending side walls 11. The container illustrated is thus similar to that of a petri dish although other shapes of containers could be used.

The base and cover are preferably formed of a transparent polymeric material and the cover generally fits loose on the base as the inside diameter of the depending side walls 11 is greater than the outer diameter of the cylindrical side wall 7. The specific material of which the container is formed may be glass but is preferably a polymeric material. Glass and polycarbonate containers will permit sterilization by autoclave and polystyrene, e.g. is sterilizable by gas, gamma radiation or ultraviolet radiation.

The present invention relates to the improved seal for sealing the cover to the base which will permit the ingress and egress of air to the dish, as illustrated, but which restricts the evaporation of the contents of the dish. In use, petri dishes are usually partially filled with a culture medium, for example agar, which is aqueous based and poured into the dishes, covered and allowed to solidify. Generally, the agar has physical characteristics which are analogous to gelatin. When used as a culture medium, the agar contains nutrients which are specific to the microorganism being grown. The agar is inoculated with the bacteria or fungi under investigation and placed in an incubator to promote growth. The air flow into the dish supplies the required oxygen for good growth and helps to prevent a deleterious accumulation of carbon dioxide which the growing microorganism produces by respiration.

Presently, the primary problem with most petri dishes is that the loose-fitting covers, which are required for the supply of oxygen to the culture, permit the rapid and relatively uncontrolled evaporation of moisture from the agar. This evaporation is detrimental to optimum culture growth and causes a decrease in the reliability of the analysis being performed. Also, the open nature of the covers does not preclude the possibility of unwanted contamination or the microorganism leaving the dish.

The seal afforded by the present invention provides the proper restrictive barrier and adheres the cover to the base of the petri dish. This seal is provided by a monolayer of a microsphere adhesive which is pressure-sensitive. The preferred adhesive is an acrylate copolymer which is described and claimed in U.S. Pat. No. 3,691,140, issued Sept. 12, 1972 to S. F. Silver, and assigned to the assignee of this application. The adhesive is described as having infusible solvent-dispersible, solvent-insoluble, inherently tacky, elastomeric copolymer microspheres consisting essentially of about 90 percent to about 99.5 percent by weight of at least one alkyl acrylate ester and about 10 to about 0.5 percent by weight of at least one monomer selected from the group consisting of substantially oil-insoluble, water-soluble, ionic monomers and maleic anhydride. The microspheres are prepared by aqueous suspension polymerization utilizing emulsifier in an amount greater than the critical micelle concentration in the absence of externally added protective colloids or the like.

The microsphere adhesive is applied to the cover in accordance with the teachings of U.S. Pat. No. 3,857,731 issued Dec. 31, 1974 to Roger F. Merrill, Jr. and Henry R. Courtney. In Merrill et al, the microsphere adhesive is mixed with a binder material that is inert toward the microspheres. When this mixture is applied to the cover, the monolayer of microsphere adhesive is formed; the structure of the monolayer comprises the binder which forms a film directly adhering to the surface of the cover, and a single layer of microspheres anchored in the binder layer. The binder quantity is such that the single layer of microspheres is anchored to the binder layer without being completely submerged in the binder. The array of the protruding portions of the microspheres presents the tacky surface which seals the cover to the base. The porosity of the seal is controlled by the lateral spacing of the microspheres, which in turn is controlled by ratio of the binder to microsphere mixture. A monolayer of microsphere adhesive formed in this manner is a microsphere retaining surface which permits repeated closure and removal of the cover without displacement of the microsphere adhesive, thereby maintaining surface tack and seal porosity. This patent is assigned to the assignee of the present application.

On a conventional size cylindrical petri dish the coating is applied to an annular area having an inside diameter of 3.15 inches and an outside diameter of 3.55 inches, providing an area of 2.11 square inches. The adhesive is coated in water and the desired dry coating weight is between 0.0035 and 0.014 gram of adhesive per square inch of area and preferably 0.007 gram per square inch.

The size of the adhesive microspheres is in a range of between about 5 and 150 microns, preferably the adhesive coating has 90 percent of the microspheres with a diameter less than 75 microns, and 10 percent less than 15 microns with the mean size in a range of 35 to 45 microns in diameter. The Silver U.S. Pat. No. 3,691,140 discloses an even broader size range for the microsphere adhesives.

To illustrate the effectiveness of the present invention it is advantageous to use a graph wherein the seal was tested as to its moisture retaining qualities against prior art sealing structures. In the graph below, the days the test dishes were stored in an incubator is plotted against the percent of weight remaining in the dish. In this chart the control dish is a conventional type of petri dish and is represented by the line A. This dish has a loose fitting cover with no seal. Line A shows the expected rapid and uncontrolled evaporation. The dishes represented by lines B and C are dishes sealed according to the prior art. Dish B is a petri dish of the same conventional type sealed with a conformable polyethylene backed pressure sensitive adhesive tape such as sold by the assignee of this application as number 483 tape and commonly sold as a sealing tape. Line B also represents a petri dish having a hermetic seal formed according to the teaching of U.S. Pat. No. 3,055,808 referred to in the introduction. Line C represents a conventional petri dish sealed with a conformable sealing beeswax. Although lines B and C show no dramatic loss of weight due to evaporation, these lines also represent seals which restrict the ingress and egress of the gases necessary for the unrestricted growth of microorganisms. Line D represents a conventional petri dish having a microsphere adhesive seal according to the preferred example of the present invention. This dish has a seal which restricts evaporation and affords suitable ingress and egress of gases necessary to maintain optimum growth of the microorganism.

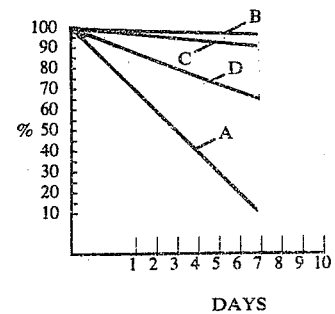

DAYS

Figure 2:
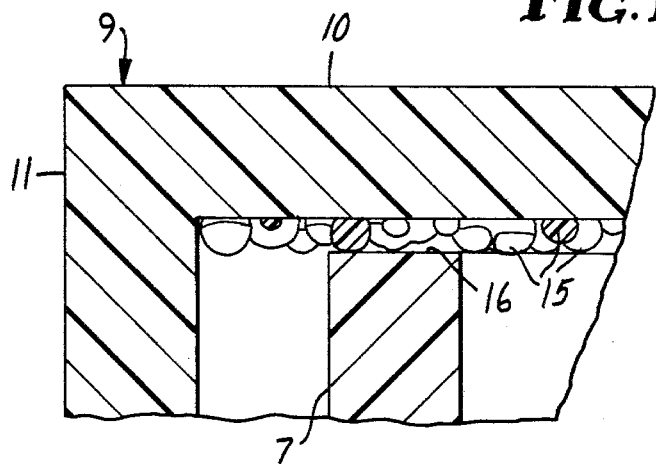
FIG. 2 is an enlarged sectional view illustrating the seal between the cover and side wall of the dish.
Figure 3:
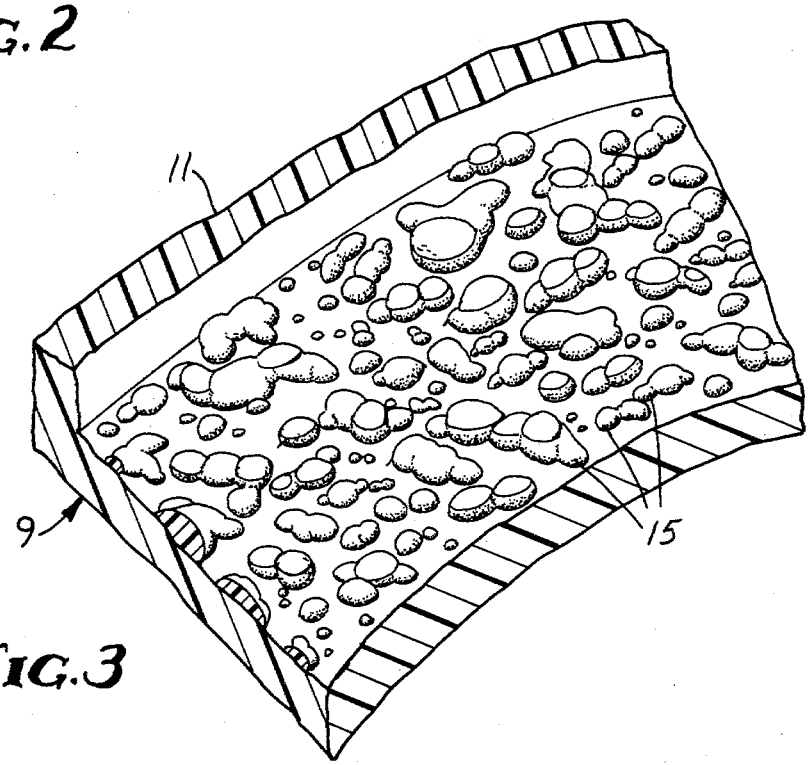
FIG. 3 is an enlarged fragmentary illustration much like a photomicrograph of the adhesive layer on the interior of the cover.

Having thus described the present invention, attention is directed to FIG. 3 illustrating an enlarged detail view of the coating of a monolayer of the elastomeric copolymer microsphere adhesive. As illustrated this microsphere adhesive forms spheres 15 which protrude from the binding adhesive and form a dense population of different sized microspheres in a random pattern across the coated area. The random size, height and placement is also illustrated in FIG. 2 which is a graphic illustration of microspheres of different diameter which are adhered to the cover 9 in a monolayer and the microspheres have sufficient inner strength that adhesion to the upper surface 16 of the side wall 7 is afforded and the adhesive bond to the side walls of the base may be released without a transfer of the adhesive from one surface to the other.

This thin adhesive coating applied to the inside cover provides the desired gaseous flow to permit the dish to serve well for laboratory investigations of various microorganisms e.g., bacteria or fungi. It maintains for the laboratory people the convenience of the non-sealed dish with an easy open and close feature but with the desired seal against evaporation.

Having thus described the present invention, what is claimed is:

1. A microbiological growth container adapted to contain a culture medium in which to cultivate one or more different microorganisms, said container comprising a base having a bottom wall and upstanding side walls, a cover having a top wall of a configuration to mate with the base and depending side walls with the inside dimension of the depending walls exceeding the outside dimension of the side walls of the base to afford a loose fit, and a monolayer of a microsphere pressure-sensitive adhesive on the inner surface of the cover adjacent the depending edge walls and exposed to and opposed to the upper surface of the side walls of the base for affording a releasable bond between the upper surface of the side walls and the cover and a permeable seal to restrict evaporation from the culture medium but affording gaseous transfer.

2. A container according to claim 1 wherein said base and cover are of transparent polymeric material.

3. A container according to claim 1 or 2 wherein said bottom wall and said top wall are circular and said base is a shallow dish.

4. A container according to claim 1 or 2 wherein said adhesive is coated directly onto the inside of said top wall to a dry coating weight of between 0.0035 grams and 0.014 grams per square inch of area.

* * * * *